(12) United States Patent
Hoke et al.

(10) Patent No.: US 9,707,000 B2
(45) Date of Patent: Jul. 18, 2017

(54) BIODEGRADABLE NERVE GUIDES

(71) Applicant: The Johns Hopkins University, Baltimore, MD (US)

(72) Inventors: Ahmet Hoke, Towson, MD (US); Shawn H. Lim, Baltimore, MD (US); Xingyu Liu, Baltimore, MD (US); Hai-Quan Mao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/081,381

(22) Filed: Nov. 15, 2013

(65) Prior Publication Data
US 2014/0081297 A1    Mar. 20, 2014

Related U.S. Application Data

(63) Continuation of application No. 12/864,493, filed as application No. PCT/US2009/000535 on Jan. 26, 2009, now abandoned.

(Continued)

(51) Int. Cl.
| | | |
|---|---|---|
| *A61B 17/11* | (2006.01) | |
| *A61L 27/38* | (2006.01) | |
| *A61L 27/48* | (2006.01) | |
| *A61L 27/52* | (2006.01) | |
| *A61L 27/54* | (2006.01) | |
| *A61L 27/56* | (2006.01) | |

(Continued)

(52) U.S. Cl.
CPC ........ *A61B 17/1128* (2013.01); *A61F 2/0063* (2013.01); *A61F 2/02* (2013.01); *A61L 27/383* (2013.01); *A61L 27/3878* (2013.01); *A61L 27/48* (2013.01); *A61L 27/52* (2013.01); *A61L 27/54* (2013.01); *A61L 27/56* (2013.01); *A61L 27/58* (2013.01); *A61L 2300/414* (2013.01); *A61L 2300/602* (2013.01);

(Continued)

(58) Field of Classification Search
CPC ......... A61B 17/1128; A61F 2230/0069; A61L 2400/12; A61L 2300/608; A61L 2430/32; A61L 27/52
See application file for complete search history.

(56) References Cited

U.S. PATENT DOCUMENTS

| 4,663,358 A | * | 5/1987 | Hyon et al. ..................... 521/64 |
|---|---|---|---|
| 2001/0029399 A1 | | 10/2001 | Ku |

(Continued)

FOREIGN PATENT DOCUMENTS

| WO | WO-2005002472 A1 | 1/2005 |
|---|---|---|
| WO | WO-2006096791 A2 | 9/2006 |

OTHER PUBLICATIONS

Zheng et al., Guidance of Regenerating Motor Axons in vivo by gradients of diffusible Peripheral nerve-derived factors, J. Neurobiol. 42:212-219, 2000.*

*Primary Examiner* — Christopher L Templeton
(74) *Attorney, Agent, or Firm* — Mintz Levin Cohn Ferris Glovsky and Popeo, P.C.; Peter F. Corless

(57) ABSTRACT

The present invention is directed to the compositions and methods of preparing hydrogel-grafted nerve guides for peripheral nerve regeneration. Particularly, the present invention describes the nerve guides and methods for preparation of hydrogel-grafted nerve guides with encapsulated neurotrophic factors and a nanofiber mesh lining the inner surface of the guide. The present invention also provides methods for peripheral nerve repair using these hydrogel-grafted nerve guides.

23 Claims, 7 Drawing Sheets

Related U.S. Application Data

(60) Provisional application No. 61/062,434, filed on Jan. 25, 2008.

(51) Int. Cl.
  *A61L 27/58* (2006.01)
  *A61F 2/00* (2006.01)
  *A61F 2/02* (2006.01)

(52) U.S. Cl.
  CPC ..... *A61L 2300/608* (2013.01); *A61L 2400/12* (2013.01); *A61L 2430/32* (2013.01); *Y10T 156/10* (2015.01); *Y10T 156/1043* (2015.01)

(56) References Cited

U.S. PATENT DOCUMENTS

| | | |
|---|---|---|
| 2001/0031974 A1* | 10/2001 | Hadlock et al. ............. 606/152 |
| 2002/0042128 A1 | 4/2002 | Bowlin et al. |
| 2003/0175410 A1* | 9/2003 | Campbell ............... A61L 27/38 427/2.24 |
| 2003/0215624 A1 | 11/2003 | Layman et al. |
| 2004/0018226 A1 | 1/2004 | Wnek et al. |
| 2005/0013844 A1 | 1/2005 | Hadlock et al. |
| 2005/0037082 A1* | 2/2005 | Wan et al. .................... 424/488 |
| 2005/0287186 A1 | 12/2005 | Ellis-Behnke et al. |
| 2006/0002978 A1 | 1/2006 | Shea et al. |
| 2006/0085063 A1 | 4/2006 | Shastri et al. |
| 2006/0184185 A1 | 8/2006 | Olausson et al. |
| 2007/0179599 A1* | 8/2007 | Brodbeck et al. ........... 623/1.44 |
| 2007/0207186 A1* | 9/2007 | Scanlon et al. .............. 424/424 |
| 2007/0269481 A1* | 11/2007 | Li et al. ....................... 424/423 |
| 2008/0038814 A1 | 2/2008 | Huie |
| 2008/0208358 A1 | 8/2008 | Bellamkonda et al. |
| 2009/0018033 A1* | 1/2009 | Morgan ............... C12N 5/0012 506/26 |

* cited by examiner

Figure 5A, Figure 5B, and Figure 5C.

BIODEGRADABLE NERVE GUIDES

RELATED APPLICATIONS

This application is a continuation application of U.S. Ser. No. 12/864,493, filed Jan. 31, 2011 (now abandoned), which is a national stage application filed under 35 U.S.C. §371 of international application no. PCT/US2009/000535, filed Jan. 26, 2009, which claims the benefit of priority under 35 U.S.C. §119(e) to U.S. Provisional Application No. 61/062,434, filed Jan. 25, 2008, each of which is incorporated herein by reference in its entirety.

GOVERNMENT SUPPORT

The following invention was supported at least in part by National Science Foundation DMR-0748340. Accordingly, the government has certain rights in the invention.

BACKGROUND OF THE INVENTION injuries to the peripheral nervous system can result in physical discontinuity of a peripheral nerve, leaving two uncoupled nerve ends, if the gap between these ends is relatively small (<20 mm), the nerve ends are surgically sutured together after which normal regenerative processes lead to eventual recovery in most cases. For larger gaps, the most successful solution currently available is the use of a sensory nerve autograft. Alongside the fact that even autografts are successful only 50% of the time, problems such as donor-site morbidity and donor nerve shortage prompt the search for alternative methods for promoting peripheral nerve regeneration.

A promising method known as nerve entubulation involves the use of hollow cylindrical chamber called nerve guide or nerve guidance channel (NGC), in which both ends of the nerve are placed. Such a nerve guide is designed to facilitate regenerating axons at the proximal nerve end to grow towards the distal end while preventing fibrous tissue infiltration or neuroma formation. It also leads to the accumulation of trophic (growth/survival promoting) and tropic (growth direction controlling) factors secreted by the distal nerve end within the guide, further encouraging effective nerve regeneration. In addition, nerve guide walls serves to mechanically ensure nerve end regeneration in the right direction.

The most important component of nerve guides is their ability to furnish a biochemical environment conducive to nerve re-growth. Such a biochemical microenvironment should include adhesion guidance signal, e.g. cell adhesion molecules and neurotrophic and tropic cues secreted by the Schwann cells. Cell adhesion cues facilitate binding and support the growth of Schwann cells and axons and thereby accelerate axonal regeneration. The latter can be provided by including or recruiting Schwann cells, or by incorporating these bioactive factors in the guides.

Incorporation of neurotrophic factors in nerve guides is a more controlled, effective, and yet complex approach. Growth factors such as NGF, BDNF, CNTF, GDNF, and FGF have been shown to elicit various different neural responses, and when combined in the right spatiotemporal profiles, they can encourage axon survival and outgrowth. The most primitive means of including growth factors into nerve guides is by filling the channel with a growth factor solution. Problems with this approach include leakage of growth factors from the nerve guide and growth factor inactivation. While continuous delivery devices such as osmotic pumps and silicone reservoirs have been used to overcome these problems, they also suffer from complications such as device failure and inflammation resulting from the non-degradable components. These considerations have propelled research focusing on delivery of growth factors using degradable polymer matrices or microcapsules. Current technologies focus on incorporating the growth factor directly into the nerve guide wall and attempting to choose a wall material that will controllably release the growth factor. Additional methods include the incorporation of growth factor in microcapsules for further tuning their release, and cross-linking growth factors directly to the scaffold material. Complications with these methods arise also, however, due to the fact that growth factor release cannot be controlled tightly; some growth factors may be toxic when delivered at a high local concentration. Even further, a problem known as the "growth-factor oasis" effect has been observed in which high levels of growth factors within the nerve guide allow axons to regenerate into the nerve guide but not out, because the regenerating axons simply become fixed to the local maximum in the growth factor concentration profile. Therefore controlling growth factor concentration and release profile in nerve guides is critical to the effectiveness of this approach.

The palette of growth factors that promote neural regeneration is well-characterized; however, what is less understood is the post-injury time frame where they have the optimal effect and the specificity of various neurotrophic factors. The poor control of neurotrophic factor encapsulation and release has been the limiting factors to develop an efficient release system to fully harness the potential benefits of local sustained release of neurotrophic factors to improve PNS regeneration.

Aligned nanofiber lining the nerve guide lumen has been shown to improve the axonal re-growth, likely though promoting the adhesion and growth of Schwann cells and/or offering guidance for axonal re-growth. In the previous nanofiber nerve guide configurations, nanofibers serve both as a guidance cue and a delivery carrier for neurotrophic factors. The complication is that a) loading neurotrophic factors with controlled dose and release kinetics has been difficult; b) growth factor loading involves organic solvent and harsh conditions, which will significantly decrease the bioactivities of the growth factors; c) it is difficult to adjust the total dose of growth factors and the nanofibers independently.

Accordingly, the need exists for more effective nerve guides for use in regeneration of for example, peripheral nerves.

SUMMARY OF THE INVENTION

The instant inventors have discovered novel nerve guides to aid in nerve growth. The novel nerve guides comprise three components: 1) a biodegradable membrane 2) a hydrogel attached to the inner surface of the biodegradable membrane, wherein the hydrogel comprises one or more neurotrophic factors; and 3) nanofibers lining the lumen of the nerve guide. One important attribute of the nerve guides of the invention is the ability to independently control the guidance function of the nerve guide by the use of nanofibers and the neurotrophic factor release function by the use of a hydrogel layer.

Accordingly, in one embodiment, the instant invention provides nerve guides comprising a hollow body in the form of a tube having a wall with an external surface and an internal surface with defines a lumen, wherein the body comprises an outer biodegradable membrane, a hydrogel layer, and a nanofiber layer wherein the lumen is surrounded by the nanofiber layer.

In one embodiment, the hydrogel layer comprises one or more neurotrophic factors, e.g., NGF, BDNF, NT3, CNTF, GDNF, FGF, pleiotrophin, osteopontin, neublastin and neurturin. In exemplary embodiments, the hydrogel layer comprises GDNF and BDNF or GDNF and NT3.

In another embodiment, the nanofibers are coated with one or more extracellular matrix molecules, e.g., laminin, fibronectin, collagen, and heparin. In exemplary embodiments, the nanofibers are coated with one or more extracellular matrix molecules selected from laminin and heparin. In a specific embodiment, the nanofiber layer comprises laminin and heparin.

In another embodiment, the biodegradable membrane is selected from a group consisting of biodegradable polyesters, poly(amino acid)s or derivatives thereof, and natural biodegradable polymers. In certain embodiments, the biodegradable membrane is between about 50 and about 1000 μm thick. In some embodiments, the biodegradable membrane is porous.

In another embodiments, the hydrogel layer is comprised of a material selected from the group consisting of PVA hydrogel or a mixture or PVA and one or more of pluronic polymers, heparin, heparan sulfate, chitosan, alginate, and dextran sulfate. In related embodiments, the thickness of the hydrogel is between about 200 μm and about 1.5 mm in its swollen state.

In another embodiment, the nanofiber layer is comprises one or more natural or synthetic biocompatible polymers, e.g., biodegradable polyesters, proteins, polysaccharides and derivatives thereof. In an exemplary embodiment, the polymer fibers comprise a polyester or derivative thereof.

In another embodiment, the polymer fibers of the nanofiber layer comprise collagen, laminin, and derivatives thereof. In another embodiment, polymer fibers of the nanofiber layer comprise chondroitin sulfate, alginate and derivatives thereof. In another embodiment, polymer fibers of the nanofiber layer comprise polylactide, polyglycolide, polycaprolactone and their copolymers thereof.

In another embodiment, the nerve guide comprises cells selected from autologous Schwann cells, Schwann cells derived from human pluripotent stem cells, and Schwann cells derived from adult stem cells. In specific embodiments, these cells are present in the nanofiber layer.

In specific embodiments, the nanofiber layer comprises electrospun fibers, e.g., randomly oriented fibers or aligned fibers. In yet another specific embodiment, the average fiber diameter is between about 10 nm and 10 μm, or between about 100 μm and 1 μm.

In another embodiment, the one or more neurotrophic factors are present in a gradient of lower concentration to higher concentration from the proximal end of the guide to the distal end of the guide.

In another aspect, the invention provides processes for making a nerve guide comprising, grafting a hydrogel onto a biodegradable polymer membrane; coating the hydrogel layer with a solution of neurotropic factors; applying a nanofiber mesh to the hydrogel surface; and forming the composition into a tube.

In specific embodiments, the biodegradable polymer membrane is formed by solvent casting, hot-pressing or stretching. In other embodiments, the grafting is thermal melt-mixing or solvent swelling.

In specific embodiment, the processes of the invention further comprise freeze-drying the neurotrophic factors in place. In specific embodiments, the step of adding a solution of neurotrophic factors and freeze drying them in place is repeated multiple time, e.g., 2-15 times. In exemplary embodiments, the neurotrophic factors are selected from the group consisting of NGF, BDNF, CNTF, GDNF, FGF, osteopontin, neublastin and neurturin.

In certain embodiments, at least two different neurotrophic factors are added to the nerve guide, e.g., at least two of GDNF, BDNF and NT3.

In other embodiments, the biodegradable membrane is selected from a group consisting of biodegradable polyesters, poly(amino acid)s or derivatives thereof, and natural biodegradable polymers.

In other embodiments, the hydrogel layer is comprised of a material selected from the group consisting of PVA hydrogel or a mixture or PVA and one or more of pluronic polymers, heparin, heparan sulfate, chitosan, alginate, and dextran sulfate.

In yet another embodiment, the nanofiber layer is comprised one or more polymers selected from biodegradable polyesters, poly(amino acid)s and derivatives thereof in specific embodiments, the nanofiber layer comprises electrospun fibers.

In another aspect, the invention provides methods of treating peripheral nerve or spinal cord injury comprising: surgically implanting a nerve guide of the invention at the site of a nerve injury; thereby treating peripheral nerve or spinal cord injury.

In another embodiment, the nerve guide comprises cells selected from autologous Schwann cells, Schwann cells derived from human pluripotent stem cells, and Schwann cells derived from adult stem cells. In exemplary embodiments, the Schwann cells are derived from human induced pluripotent stem cells and human embryonic stem cells. In another exemplary embodiment, the Schwann cells are derived from allogenic or autologous mesenchymal stem cells.

DESCRIPTION OF THE DRAWINGS

(FIG. 5C). Percentage of neuronal commitment (Tuj1+ cells) of NSCs cultured on various substrates

DETAILED DESCRIPTION OF THE INVENTION

Figure 1:
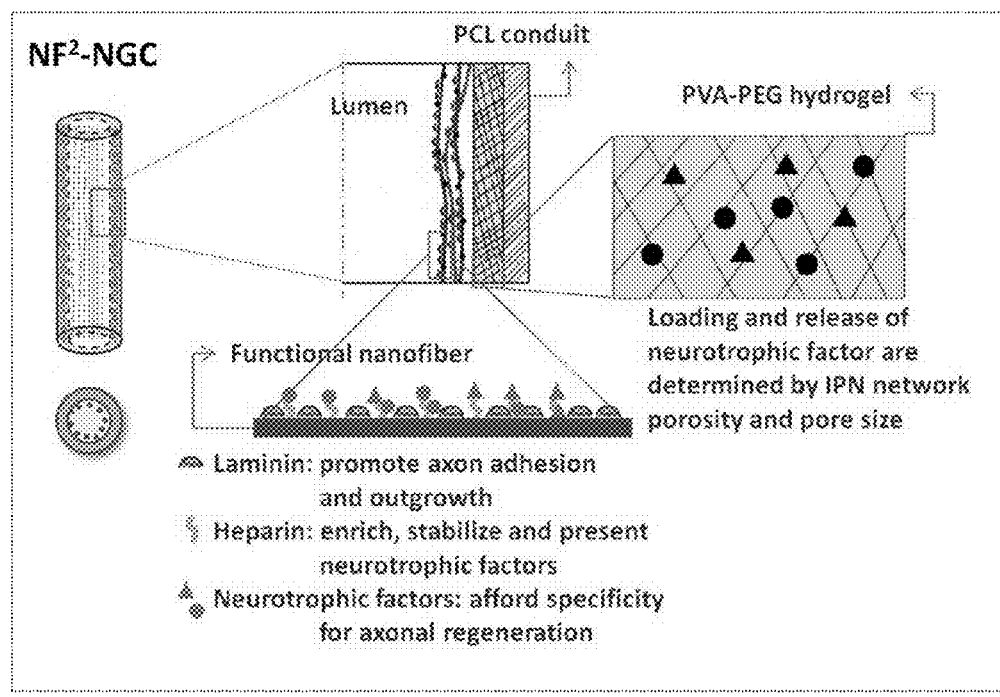
FIG. 1 is a schematic of the design of a hydrogel-grafted nerve guide with nanofibers lining the lumen of the guide.

The present invention is directed to the composition and preparation of hydrogel-grafted nerve guides for peripheral nerve regeneration. Particularly, the present invention describes the nerve guides and methods for preparation of hydrogel-grafted nerve guides with encapsulated neural trophic factors and a nanofiber mesh lining the inner surface of the guide. The present invention also provides methods for peripheral nerve repair using these hydrogel-grafted nerve guides.

The following abbreviations are used in the specification and for clarity are set forth here: PCL: poly(ε-caprolactone); PCLEEP: poly(ε-caprolactone-co-ethyl ethylene phosphate); PEG: poly(ethylene glycol); PGA: poly(glycolide); PLA: poly(lactide) PLGA: poly(lactide-co-glycolide); PVA: polyvinyl alcohol); PVA-83k-99: PVA with molecular weight of approximately 85,000-146,000 and degree of hydrolysis 99%; PVA-124k-98: PVA with molecular weight of approximately 125,000-186,000 and degree of hydrolysis 98%; PNS: peripheral nervous system and ECM: extracellular matrix.

As used herein, the term "hydrogel" is intended to mean a colloidal gel in which water is the dispersion medium. In the instant invention, hydrogels are used as a component of the nerve guides. The hydrogel layers of the nerve guides of the invention comprise one or more neurotrophic factors and release the factors over a period of time. Exemplary hydrogels of the invention include PVA hydrogel or a mixture or PVA and one or more of pluronic polymers, heparin, heparan sulfate, chitosan, alginate, and dextran sulfate. In certain embodiments of the invention, the hydrogels of the invention are FDA approved for therapeutic use in human beings.

As used herein the term "biodegradable" is intended to mean a layer that is capable of decaying through the action of living organisms. In specific embodiments, the term biodegradable is in reference to a layer that is on the outside of the nerve guides of the invention. Exemplary biodegradable compositions include biodegradable polyesters, poly (amino acid)s or derivatives thereof, and natural biodegradable polymers.

As used herein, the term "electrospinning" is intended to mean a process that uses an electric field to draw a solution comprising, for example, a polymer or a ceramic from the tip of the capillary to a collector. A high voltage DC current is applied to the solution which causes a jet of the solution to be drawn towards the grounded collector screen. Once ejected out of the capillary orifice, the charged solution jet gets evaporated to form fibers and the fibers get collected on the collector. The size and morphology of the fibers thus obtained depends on a variety of factors such as viscosity of the solution, molecular weight, nature of the polymer or ceramic and other parameters regarding the electrospinning apparatus. The electrospinning process to form polymer nanofibers has been demonstrated using a variety of polymers (Huang, et al. Composites Science and Technology 2003; 63). Exemplary polymers used in electrospinning methods of the invention include those disclosed in U.S. Pat. No. 6,852,709, issued Feb. 8, 2005. Electrostatic spinning is a process by which polymer fibers of nanometer to micrometer size in diameters and lengths up to several kilometers can be produced using an electrostatically driven jet of polymer solution or polymer melt. The polymer solution or melt may comprise one or more therapeutically active molecules at concentrations determined by the ordinary skilled artisan.

The term "treated," "treating" or "treatment" includes the diminishment or alleviation of at least one symptom associated or caused by the state, disorder or disease being treated. Moreover, treatment includes the partial or complete regeneration of nerve fibers in a subject.

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

As used herein, the term "uniaxial electrospinning" is intended to mean the electrospinning of a single electrospinning solution supply that is dispensed from a single spinneret.

As used herein, the term "coaxial electrospinning" is intended to mean the electrospinning of a single electrospinning solution supply that comprises of two different solutions that are physically separated from each other and that are dispensed from two separate spinnerets that share the same axis of symmetry.

As used herein, the term "multiaxial electrospinning" is intended to mean the electrospinning of a single electrospinning solution supply that comprises of multiple solutions that are physically separated from each other and that are dispensed through multiple spinnerets that share the same axis of symmetry.

As used herein, the term "polymer" generally includes, but is not limited to, homopolymers, copolymers, such as for example, block, graft, random and alternating copolymers, terpolymers, etc., and modifications thereof. In addition, unless otherwise specifically limited, the term "polymer" also includes all possible geometric configurations of the molecule. In specific embodiments, the polymers used in the compositions of the invention are polyesters. An exemplary polyester used in the compositions of the invention is PCLEEP.

As used herein, the term "poly (ε-caprolactore-co-ethyl ethylene phosphate (PCLEEP)" is intended to mean a polymer described in U.S. Pat. No. 6,852,709 having the following structure:

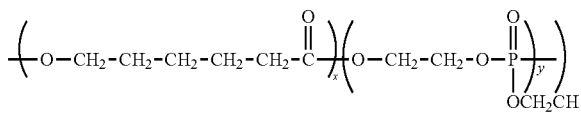

As used herein, the term "tube" is intended to mean composition of matter having an interior surface, and exterior surface, a lumen and openings on the two ends. The tubes of the invention may be as described herein.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymeric materials of the invention, biocompatible refers to the ability of the polymeric material (or polymeric materials) to be accepted by and to function in its intended manner in a recipient.

As used herein, "therapeutically effective amount" refers to that amount of a therapeutic agent, e.g., a neurotrophic factor, that produces the desired effect in a subject. In some aspects, the phrase refers to an amount of neurotrophic factor that, when incorporated into a nerve guide of the invention, induces growth of a nerve. A physician or veterinarian of ordinary skill can readily determine the effective amount of the neurotrophic factor required.

As used herein, the term "extracellular matrix molecules" is intended to mean molecules that are naturally found in the extracellular matrix of biological tissue. Extracellular matrix molecules are produced intracellularly and secreted into the extracellular matrix via exocytosis. Once secreted these molecules aggregate with the existing matrix. Exemplary extracellular matrix molecules used in the nerve guides of the invention include laminin, fibronectin, collagen, and heparin.

Nerve Guides

The instant application provides novel nerve guides that contains three key components: 1) a biodegradable membrane; 2) a PVA-based cryogel grafted onto the inner surface serving as the delivery carrier, in which the growth factors are incorporated; 3) nanofibers lining the lumen of the nerve guide, serving as the guidance cue for cell adhesion and growth.

The biodegradable membrane is comprised of biodegradable polyesters (e.g. PLA, PGA, PCL and their copolymers), poly(amino acid)s and their derivatives, natural biodegradable polymers (e.g. chitosan, collagen, alginate esters, and their derivatives). The thickness of the membrane ranges from 50 to 1000 µm and the inner diameter of the tube ranges from 0.5 to 5 mm. The membrane can be non-porous or porous with pore size of less than 2 µm.

The hydrogel layer is comprises of polyvinyl alcohol (PVA) hydrogel or a hydrogel of PVA in combination with a polymer selected from a list consisting of Pluronic polymers, heparin, heparan sulfate, chitosan, alginate, and dextran sulfate. The thickness of the PVA layer grafted onto the biodegradable membrane ranges from 200 µm to 1.5 mm in the swollen state. The degree of crosslinking can be controlled by polymer molecular weight, concentration, composition, as well as the number of free-thaw cycles, freezing temperature and time. The hydrogel layer can also comprise multiple layers of gels, e.g., cryogels, of different compositions.

The nanofiber layer is applied on top of the hydrogel layer. The nanofibers are composed of biodegradable polymers that degrade over a period of time ranging from 3 weeks to 3 months. Example polymers include PCL, PGA, PLA, polyphosphate, and their copolymers, or collagen fibers. The nanofiber layer can comprise nanofibers that are surface-functionalized to improve the cell adhesion property and enhance the local enrichment, stabilization and presentation of neurotrophic factors. For example, polycaprolactone-co-ethyl ethylene phosphate (PCLEEP) nanofibers can be coated with collagen or fibronectin or laminin solution before laid onto the hydrogel layer. Nanofiber surface can also be grafted with heparin or heparan sulfate, which serves to recruit, bind and present growth factors to axons.

The nerve guides of the invention are comprised of FDA-approved polymers for in vivo implantation. Exemplary polymers include of PVA, PEG and PCL.

A specific example is shown in FIG. 1. This hydrogel-grafted nerve guide includes a biodegradable PCL nerve guide, a poly(vinyl alcohol) hydrogel grafted to PCL nerve guide luminal surface serving as the carrier for neurotrophic factors, and functionalized nanofibers with surface-tethered laminin and heparin as an axonal guidance cue with neurotrophic factor presentation capability. PVA, PEG and PC, are FDA-approved polymers for in vivo implantation.

Methods of Making Nerve Guides

The nerve guides of the invention can be produced any number of way that are know to those of skill in the art. Exemplary methods for producing the nerve guides of the invention are set forth below.

In one embodiment, the invention provides a method for making nerve guides comprising grafting a PVA layer to a polymer membrane prepared by either solvent casting, hot-pressing or stretching. The grafting can be achieved by thermal melt-mixing or solvent swelling.

In one exemplary embodiment, a hydrogel layer, e.g., PVA, is grafted to a biodegradable membrane, e.g., a PCL membrane, by heating biodegradable membrane at a temperature between 80 and 120° C., followed by covering the membrane surface with a 0.1 to 5% solution of hydrogel in water (0.5 to 1.5 mL per 10 $cm^2$) for 10 to 60 minutes, followed by quenching the film to −20° C. for 10 to 60 minutes. In an alternative process, the biodegradable membrane is heated with 0.1 to 5% of hydrogel solution at 70 to 95° C. for 10 to 60 minutes, followed by quenching the film to −20° C. for 10 to 60 minutes.

One important advantage of this exemplified method is that it does not involve the use of organic solvent or extreme conditions. It only involves the use of aqueous medium and temperatures at or below room temperature. Such a process has several distinct advantages: a) it can better preserve the bioactivities of the growth factors loaded; b) it is convenient to incorporate multiple growth factors and easy to control the relative doses of these factors.

In another example, the hydrogel grafting can be achieved by swelling the biodegradable membrane with tetrahydrofuran (THF, 50 to 200 µL per 10 $cm^2$) for 1 to 5 minutes at room temperature, then adding 0.1 to 5% PVA solution (0.5 to 1.5 mL per 10 $cm^2$) and incubating for 10 to 60 minutes, followed by quenching the film to −20° C. for 10 to 60 minutes.

Hydrogels are loaded with one or more neurotrophic factors. Exemplary neurotrophic factors include NGF, BDNF, NT3, CNTF, GDNF, FGF, pleiotrophin, osteopontin, neublastin and neurturin. Combinations of neurotrophic factors are contemplated to be included in the nerve guides of the invention. Moreover, gradients of neurotrophic factors can be loaded into the nerve guides. Altering the biological properties of the hydrogel, e.g., the hydrogel pore size, can modulate the release of the neurotrophic factors.

In exemplary embodiments, hydrogel coating and loading of bioactive molecules is done according to the following steps: a) the biodegradable membrane is warmed up to 4 to 20° C., dependent on the stability of bioactive molecules, washed with, for example, water or phosphate buffered saline (PBS); b) the biodegradable membrane is then loaded with a hydrogel solution (5 to 20% in water or PBS, 0.5 to 1.5 mL per 10 cm$^2$) containing bioactive molecules, e.g., neurotrophic factors, at a concentration of 0.1-100 μg/ml; c) the construct is then frozen for 2 to 72 hours at a temperature between −80 to 0° C.; d) the construct is subsequently warmed to room temperature for 30° C.; e) Steps c) and d) will be repeated for 2 to 15 times in order to achieve the desired concentration of neurotrophic factors or to establish the desired gradient of neurotrophic factors.

After the biodegradable layer and hydrogel layer are grafted, and the hydrogel layer is loaded with one or more neurotrophic factor, a nanofiber layer is attached to the lumen side of the hydrogel layer.

In an exemplary embodiment, the nanofiber layer is comprised of electrospun polymer.

Electrospun nanofiber layers described herein can be made using electrospinning methods that are well known in the art and can be preformed using only routine experimentation.

Specifically, a charged solution comprising, for example, a polymer is fed through a small opening or nozzle (usually a needle or pipette tip). Due to its charge, the solution is drawn toward a grounded collecting plate, e.g., a metal screen, plate, or rotating mandrel, typically 5-30 cm away, as a jet. During the jet's travel, the solvent gradually evaporates, and a charged fiber is left to accumulate on the grounded target. The charge on the fibers eventually dissipates into the surrounding environment. If the target is allowed to move with respect to the nozzle position, specific fiber orientations (aligned or random) can be achieved.

The nanofiber mesh can be surface modified with one or more extracellular matrix proteins in order to enhance nerve growth into and through the nerve guide. Exemplary extracellular matrix proteins include laminin, fibronectin, collagen, and heparin. In one embodiment, the nanofiber layer is coated with one or both of laminin and heparin. One other group of molecules that can be applied to the nanofibers is cell adhesion molecules such as, for example, integrins and NCAMs.

In a specific embodiment, a layer of nanofiber mesh is laid over the hydrogel surface. The construct is then lyophilized. The construct is subsequently roiled up into tubes with an appropriate inner diameter, for example 0.5 to 5 mm, and tube is sealed with the application of sealant or a solvent for the membrane and dried under vacuum. The tubes are cut into an appropriate length and stored until use.

In one specific example, a layer of random nanofiber mesh of PCLEEP electrospun fibers is laid onto PVA hydrogel before being lyophilized at −20° C. The layers are then rolled into a tube around a 2-mm mandrel, and the tube is then sealed with 5 μL of dichloromethane for each 1-cm length, and dried at 4° C. under vacuum over night.

In certain embodiments of the invention, specific types of cells can be loaded onto the nanofiber layer prior to the implantation to enhance the regeneration outcomes. The nerve guides may contain bioactive molecules, e.g., neurotrophic factors, in certain embodiments, the nerve guides do not contain bioactive molecules, e.g., neurotrophic factors. In other embodiments, nerve guides comprise cells selected from the group consisting of isolated and purified Schwann cells, Schwann cells or their precursors derived from human embryonic stem cells or adult stem cells, such as neural crest stem cells, and Schwann cell lines derived from the above sources.

Therapeutic Use

The new nerve guides of the invention can be used directly to improve regeneration of peripheral nerves. They can also be used to promote spinal cord regeneration when proper growth factors are loaded, where the sealing of the tube can be achieved in situ with tissue-compatible sealant.

In specific embodiments, the nerve guides of the invention are surgically implanted in a subject by a trained physician. For example, nerve guides of the invention can be implanted in a desired location using a suitable surgical procedure. Suitable surgical procedures are described, for example, in Hadlock et al., Archives of Otolaryngology—Head & Neck Surgery 124:1081-1086, 1998; WO 99/11181; U.S. Pat. No. 5,925,053; WO 88/06871; Wang et al., Microsurgery 14:608-618, 1993; and Mackinnon et al., Plast. Reconst. Surg. 85:419-424, 1990.

The nerve guides can be used to promote specific type of nerve regeneration when a proper combination of neurotrophic factors is incorporated in the hydrogel layer. For example, a nerve guide with pleiotrophin can be used to promote motor nerve regeneration.

EXAMPLES

It should be appreciated that the invention should not be construed to be limited to the examples that are now described; rather, the invention should be construed to include any and all applications provided herein and all equivalent variations within the skill of the ordinary artisan.

Example 1

Preparation of a Nerve Guide

1) Cast a 10 cm$^2$ film of 50:50 PCl/PCLEEP on top of a glass slide mold from a 12% wt solution in dichloromethane.
2) Dry the film under vacuum over night to remove residual solvent.
3) Place slide on a hot plate and heat the film to 100° C.
4) Add 1 ml of 1% PVA in water on top of the film.
5) Quench the film at −20° C. for 30 minutes.
6) Add 500 μL of 5% PVA containing 5 μg GDNF on top of the film.
7) Freeze the composite at −20° C. for 12 hours.
8) Cool at 25° C. for 30 minutes.
9) Freeze the composite at −20° C. for 2 hours.
10) Cool at 25° C. for 30 minutes.
11) Repeat steps 9 and 10 for a total of 12 cycles.
12) Freeze-dry the construct.
13) Place electrospun PCL nanofibers modified with laminin on top of the hydrogel layer.
14) Roll the construct into a tube with inner diameter of 3 mm and the hydrogel layer on the luminal side.
15) Seal the membrane with a trace quantity of 20% solution of PCL in dichloromethane.
16) Cut the tube to the desired length.

Example 2

Release Profile of Model Proteins from the Nerve Guide Construct

Figure 2:
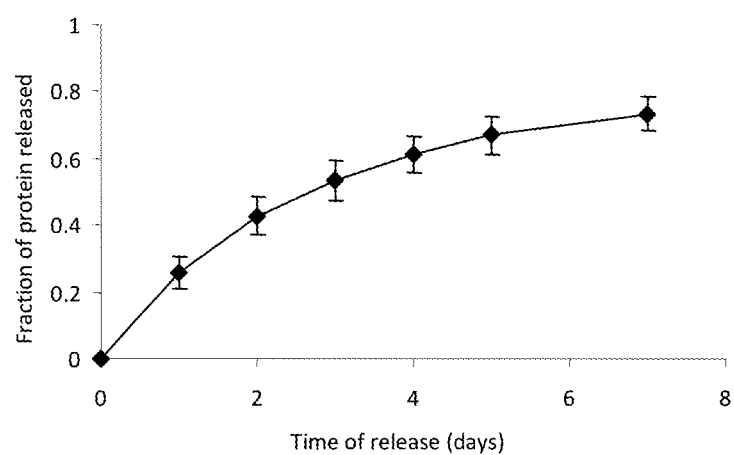
FIG. 2 depicts the release profile of bovine serum albumin (BSA) as a model protein factor loaded in a 5% PVA-83k-99 hydrogel construct into buffered saline at 37 CC.

A nerve guide is prepared as described in Example 1 with bovine serum albumin (BSA) as a model protein factor loaded in a 5% PVA-83k-99 hydrogel construct into buffered saline at 37° C., gel was frozen at −2° C. for 72 hours, followed by 4 conventional freeze-thaw cycles. The release profile of BSA is shown in FIG. 2.

Example 3

Process of Preparing a Double-Layered Hydrogel Nerve Guide

1) Repeat steps 1-8 as described in Example 1 with Gel A loaded onto the PCL membrane.
2) Independently prepare a 0.5 mm thick PVA hydrogel (Gel B) by replicating steps 6-11 as described in Example 1, with the sole modification of omitting the growth factor loading.
3) Add 50 µL of 5% PVA solution on top of Gel A, then lay Gel 13 on top of the solution.
4) Repeat steps 9 and 10 as described in Example 1 for a total of 4 cycles.
5) Continue with steps 12-16 as described in Example 1.

Other modifications can be used to modify the rate of release of proteins from the hydrogel. The addition of a protein-free top layer provides an additional diffusion barrier to incorporate time-delayed protein release. Blending PVA with other water-soluble small molecular weight polymers changes the hydrogel crystallinity. Changing the number of freeze-thaw cycles, or simply incubation for prolonged periods at sub-zero temperatures modulates the initial burst release from the hydrogel. Incorporation of heparin into the hydrogel helps to bind and retain growth factors within the matrix.

Example 4

Figure 3:
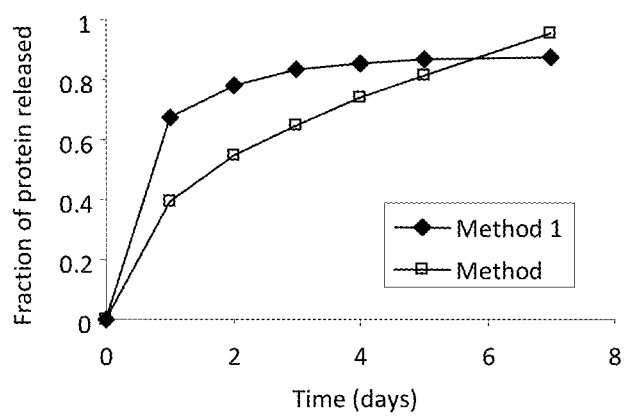
FIG. 3 depicts the release profile of two nerve guide are prepared according to a procedure described in Example 1 with BSA as a model protein factor loaded in a 5% PVA-124k-98 hydrogel prepared under two different processing conditions. The first method involves continuous freezing at 2° C. for 8 hours; and the second method involves continuous freezing at −2° C. for 36 hours. Prolonged sub-zero freezing times results in lower burst release of protein and a more sustained release profile over one week.

Release Profile of Protein Factor from PVA Hydrogel-Grafted Nerve Guides Processed Under Different Conditions Two nerve guides are prepared according to a procedure described in Example 1 with BSA as a model protein factor loaded in a 5% PVA-124k-98 hydrogel prepared under two different processing conditions: Method 1) continuous freezing at −2° C. for 8 hours; Method 2) continuous freezing at −2° C. for 36 hours. Prolonged sub-zero freezing times results in lower burst release of protein and a more sustained release profile over one week. The release profiles are shown in FIG. 3.

Example 5

Figure 4:
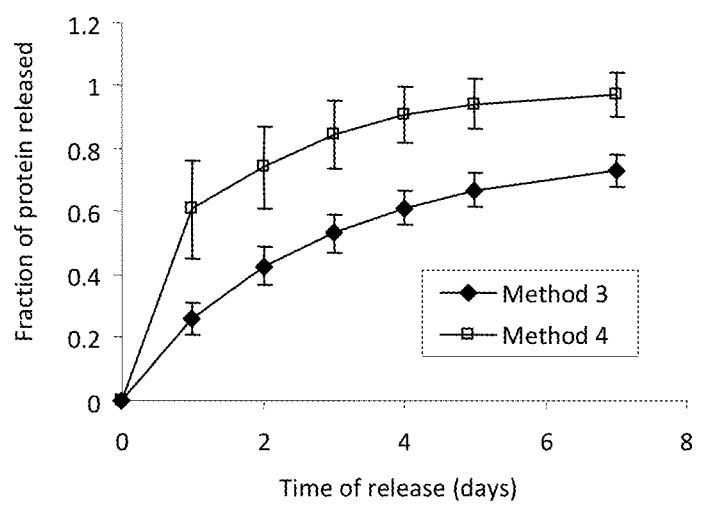
FIG. 4 depicts the release profiles of two nerve guides prepared according to a procedure described in Example 1 with BSA as a model protein factor loaded in a 5% PVA-83k-99 hydrogel matrices prepared under two different processing conditions. Method 3) the hydrogel is frozen at −2° C. for 72 hours, followed by 4 conventional freeze-thaw cycles; Method 4) the hydrogel prepared with 10 conventional freeze-thaw cycles. The solid diamonds represent BSA release from nerve guides prepared according to method 3, and open squares represent BSA release from nerve guides prepared according to method 4.

Release Profile of Protein Factor from Another Set of PVA Hydrogel-Grafted Nerve Guides Processed Under Different Conditions Two nerve guides are prepared according to a procedure described in Example 1 with BSA as a model protein factor loaded in a 5% PVA-83k-99 hydrogel matrices prepared under two different processing conditions. Method 3) the hydrogel is frozen at −2° C. for 72 hours, followed by 4 conventional freeze-thaw cycles; Method 4) the hydrogel prepared with 10 conventional freeze-thaw cycles. The release profiles are shown in FIG. 4, where solid diamonds represent BSA release from nerve guides prepared according to method 3, and open squares represent BSA release from nerve guides prepared according to method 4.

Example 6

Optimization of Release Kinetics of the Neurotrophic Factors and the Nanofiber Surface Functionality of the Nerve Guides The nerve guide design allows examination of the two parameters/functionalities independently. We will first investigate how trophic factor release kinetics and dose will impact the quality and speed of the axon regeneration using GDNF as a model trophic factor, as our previous study demonstrated that GDNF is one of the most effective neurotrophic factors for peripheral nerve regeneration. Adopting the most effective GDNF loading configuration, we will then evaluate the effects of nanofiber surface functionality (laminin coating and heparin-tethers) and alignment (axially aligned and randomly coated) on axon re-growth.

Optimization of Neurotrophic Factor Release Kinetics and Dose

The temporal release of neurotrophic factors from the hydrogel layer, e.g. the timing of peak release and the overall duration of release, are controlled by the pore size/crystallinity of the PVA cryogels. The peak concentration of the trophic factor should ideally coincide with the time frame during which cells are most receptive. The duration of release may need to cover the entire time period during which cells upregulate the appropriate receptors. We have shown that PVA molecular weight, concentration, and processing parameters (cycle and temperature) are important factors determining pore size, and thus the diffusivity of trophic factors through the hydrogel. We will first identify the most efficient local delivery profile for GDNF by examining the GDNF dose and release duration. In this study, nerve guides without nanofiber lining will be used. In preliminary studies, we will first perform in vitro neurite outgrowth assays into the nerve guides with different GDNF doses and release kinetics (Mi et al., 2007). These assays will utilize spinal cord explants with different nerve guides placed in front of the ventral roots; after 1-2 weeks of outgrowth into the nerve guides, cultures will be fixed, stained for neurofilament heavy chain and axons regenerating into the nerve guides will be counted. Once the nerve guides are optimized in vitro, we will move into in vivo studies. The following table lists two potential different concentration and release kinetics options to be tested in vivo. The exact loading amount and the release duration will be guided by the in vitro assays.

| Group # | GDNF dose | Target release duration |
| --- | --- | --- |
| 101 | 0.6 µg | 3 weeks |
| 102 | 0.6 µg | 1 week |
| 103 | 0.2 µg | 3 weeks |
| 104 | 0.2 µg | 1 week |
| 105 | 0 (without GDNF) | 0 |
| 106 | Positive control - collagen nerve guides (NeuraGen) | |

These nerve guides (#101-105) will be prepared and GDNF release kinetics in phosphate buffer at 37° C. will be characterized by ELISA; and GMT bioactivity will be analyzed by neurite outgrowth assay (Chew et al., 2005; Chew et al., 2007). These nerve guides will be evaluated in the rat sciatic nerve transection model (Chew et al., 2007). The nerve regeneration outcomes will be correlated with GDNF release kinetics.

Optimization of Nanofiber Configuration (Surface Functionality and Alignment)

Figure 5:
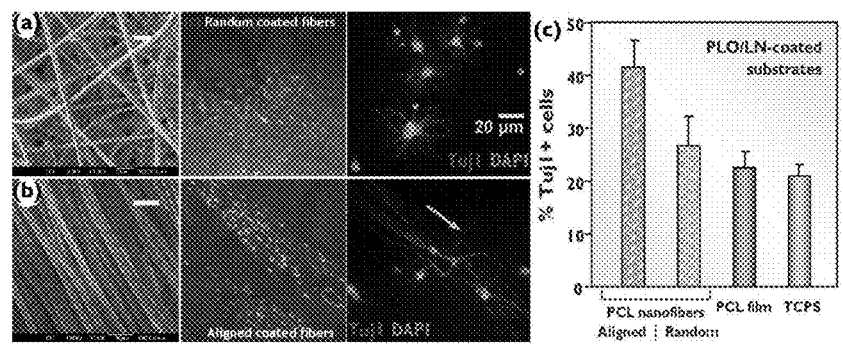
FIG. 5 depicts at neural stem cells (NCS) differentiated on (FIG. 5A) random and (FIG. 5B) aligned LN-coated PCL nanofibers. The average fiber diameter is 250 nm. NSCs were cultured in the presence of 0.5% fetal bovine serum and 0.5 μM retinoic acid for 6 days. Differentiated cells formed extended long processes along fiber axis. Fibers provided guidance cue for process extension and outgrowth. Arrow in (b) indicates the axis of aligned fibers.

Axonal growth cones are guided to their targets by contact-guidance mechanism or by diffusible chemotropic factors. The adhesion guidance function of the nanofibers can be improved by surface conjugating relevant adhesion molecules. We have demonstrated that the adhesion property of nanofibers can be dramatically improved by surface functionalization (Jiang et al., 2006; Fischer et al., 2007). Laminin (LN) has been identified as an effective matrix molecule that mediates the adhesion and migration of axons and Schwann cells. Of particular interest to this study is a set of LN-coated PCL or PCLEEP nanofibers showing effective support for neural stem cell adhesion and alignment along the axis of the nanofibers (FIG. 5) (Chua et al., 2007). This alignment promotes the neuronal differentiation of neural stem cells (NSCs) significantly. Therefore, LN-coated nanofibers should provide additional benefit for axonal guidance. It is also likely that these nanofibers provide the initial adhesion and survival of Schwann cells inside the nerve guides. Another critical function lacking in the typical nerve guides is the local retention and presentation of neurotrophic factors to axons and/or Schwann cells. Studies have shown that heparan sulfates in the basal lamina serves as an anchor to recruit, enrich, stabilize and present growth factors and trophic factors (Barnett et al., 2002; Rider, 2006). The majority of neurotrophic factors (e.g. PTN, GDNF, BDNF, NT-3, neuregulin, midkine) exhibit high heparin-binding activity. The stability and bioactivity of these trophic factors can be enhanced by "local" presentation through heparin binding. We will conjugate heparin and LN to nanofiber surface hence providing both adhesion guidance and trophic factor presentation functions, and load these nanofibers to the optimized nerve guides. This new generation of nerve guides will then be tested in the rat sciatic nerve transection model. Prior to moving into animal model, concentration of LN and HP will be optimized with in vitro axon regeneration assays as described above. The following nerve guides groups will be tested.

| Group # | Neurotrophic factor GDNF dose | Nanofiber Surface functionality | Alignment |
|---|---|---|---|
| 201 | 0.02 to 100 micrograms | LN | Aligned |
| 202 | 0.02 to 100 micrograms | LN | Random |
| 203 | 0.02 to 100 micrograms | LN-HP | Aligned |
| 204 | 0.02 to 100 micrograms | LN-HP | Random |
| 205 | 0.02 to 100 micrograms | HP | Aligned |
| 206 | 0.02 to 100 micrograms | Unmodified | Aligned |

We will identify the most efficient neurotrophic factor delivery profile, and confirm whether aligned nanofibers, i.e. directional guidance, will promote the vigor and speed of nerve regeneration in comparison with random fibers. We will also determine if synergy exists between locally released neurotrophic factor(s) and nanofiber guidance cue.

Example 7

To Afford Subtype Specificity to the New Nanofiber Nerve Guides by Incorporating Specific Sets of Neurotrophic Factors Growth factors such as NUT, BDNF and GDNF have been implicated to preferentially promote sensory axon outgrowth, whereas motor axons are shown to respond better to PIN, VEGF and GDNF. Most of current approaches have focused on incorporation of single growth factors within nerve guides. Based on our previous studies on motor versus sensory Schwann cells (Hoke et al., 2006), we expect that a combination of trophic factors can elicit both faster and better nerve recovery, and may yield re-growth of specific type of nerves (motor vs. sensory nerves). We will use the best nanofiber nerve guide configuration identified from Example 6 to incorporate neurotrophic factor specificity into these nerve guides by loading different sets of trophic factors that have demonstrated nerve subtype specificities.

| Test Group # | Neurotrophic factor(s) |
|---|---|
| 301 | GDNF |
| 302 | NGF |
| 303 | PTN |
| 304 | NGF + GDNF |
| 305 | PTN + GDNF |

These nerve guides will be evaluated in our traditional models of nerve repair and regeneration in the rat femoral nerve (Madison et al., 1996; Brushart et al., 1998; Redett et al., 2005). We will evaluate whether nerve guides loaded with different sets of neurotrophic factors will lead to preferential re-growth of specific subtype nerves. We will evaluate the success of motor versus sensory regeneration by retrogradely labeling the axons that regenerate through nerve guides and counting the number of motor and sensory neurons in the spinal cord and DRG, respectively.

We will demonstrate whether local release of pro-motoneron vs. pro-sensory neuron trophic factors will afford subtype specificity for the regenerated nerve Example 8

Figure 6:
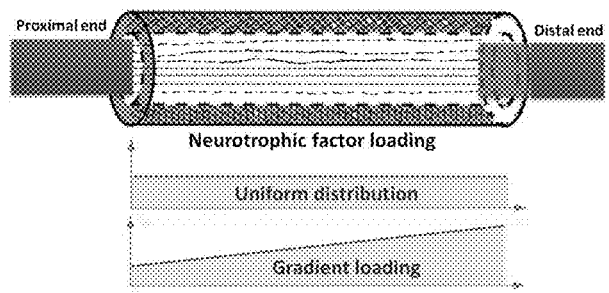
FIG. 6 depicts loading of neurotrophic factors in nanofiber nerve guides (either nanofiber loaded or not).

To Incorporate Gradient Loading of Neurotrophic Factor(s) and Demonstrate its Advantage of Enhancing Nerve Regeneration Ample evidence exists that suggest that axons are responsive to gradients of trophic cues. For example, in the developing spinal cord, axons respond to gradients of chemoattractants such as netrin-1, often over fairly long distances. Other in vitro experiments with neurons harvested from the dorsal root ganglion have demonstrated a similar response to gradients of neurotrophic cues such as NGF, or extracellular matrix cues such as laminin. Within the context of repairing the transected peripheral nerve, it is similarly possible that axons projecting from the proximal end of the injury can be induced to grow into the nerve guide, along its length and towards the distal stump by the presence of a high trophic concentration at the distal end. We hypothesize that a gradient release of neurotrophic factors will further enhance the regeneration outcome. This hypothesis will be tested by preparing nerve guides with growth factor gradients incorporated within the tube walls. We will develop a loading method to create trophic factor gradients with higher neurotrophic factor loading at the distal end and lower loading at the proximal end (FIG. 6). Such a loading configuration will ensure that the released neurotrophic factor remains in effective concentration range at the distal end by the time the regenerated axon reaches there; it also mimics the situation where neurotrophic factors are released from the Schwann cells from the injured distal nerve end, possibly creating a gradient chemotactic cue to guide regeneration.

The most effective motoneuron promoting nerve guide configuration identified in Examples 6 and 7 will be used for this study. We will load the neurotrophic factor(s) at the prescreened total concentration in uniform and gradient loading, respectively. We will characterize the neurotrophic factor distribution by incorporating a fluorescently labeled neurotrophic factor during the loading step, and imaging the nerve guide wall on a confocal fluorescence microscope.

The dissipation of the protein as well as tracking the persistence of the gradient can be achieved by measuring the fluorescence intensity on fluorescent micrographs and correlating to a known standard curve. It is important that the gradient of growth factor ultimately dissipates, so that the regenerating axon has impetus to exit the distal end of the tube to reconnect with the damaged distal nerve stump. We will then evaluate the effect of gradient loading/release on nerve regeneration by testing the following groups.

| Group # | Trophic factor loading | Nanofiber functionality | Trophic factor Gradient pattern |
|---|---|---|---|
| 401 | Example 6 & 7 | Example 6 | Ascending gradient |
| 402 | | Example 6 | Uniform distribution |
| 403 | Example 6 & 7 | " | Descending gradient |
| 404 | Positive control - collagen nerve guides | | |

These nerve guides will be evaluated in the rat sciatic nerve repair model as done previously. We will evaluate the success of nerve regeneration by retrogradely labeling the axons that regenerate through nerve guides and counting the number of motor and sensory neurons in the spinal cord and DRG, respectively.

We will determine whether gradient release will improve the quality and speed of nerve re-growth, Example 9

Efficacy of Nerve Guides Having GDNF Loaded onto the PVA-Hydrogel Matrix

Figures 7A, 7B:
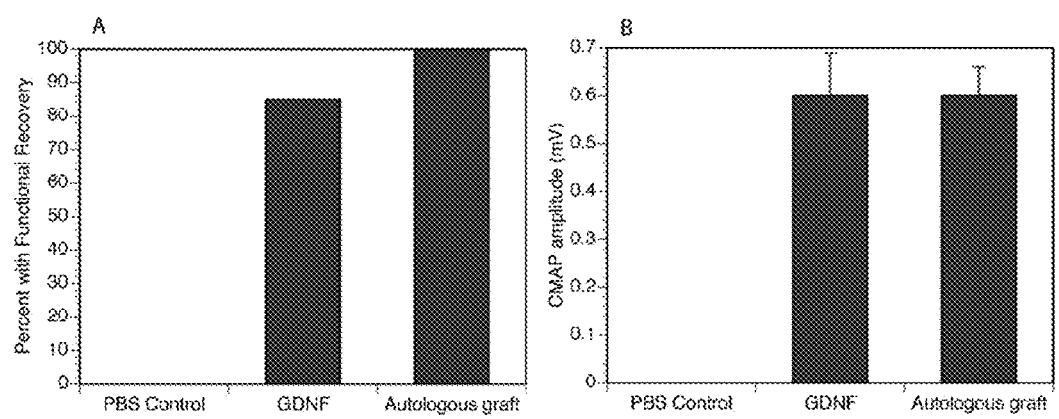
FIG. 7 depicts adult rat sciatic nerves were transected at the mid thigh section and repaired with nerve guides with nanofibers in which GDNF was loaded onto the PVA-hydrogel matrix. After 3 months, animals were evaluated for functional recovery (FIG. 7A) and emergence of compound motor action potentials (CMAP) in the sciatic nerve innervated foot muscles (FIG. 7B). GDNF-loaded nerve guides with nanofibers were similar to autologous nerve grafts and superior to PBS-loaded empty tubes.

FIG. 7 depicts adult rat sciatic nerves that were transected at the mid thigh section and repaired with nerve guides with nanofibers in which GDNF was loaded onto the PVA-hydrogel matrix. After 3 months, animals were evaluated for functional recovery (A) and emergence of compound motor action potentials (CMAP) in the sciatic nerve innervated foot muscles (B). GDNF-loaded nerve guides with nanofibers were similar to autologous nerve grafts and superior to PBS-loaded empty tubes.

References for Examples 6-8

Barnett M W, Fisher C E, Perona-Wright G, Davies J A (2002) Signalling by glial cell line-derived neurotrophic factor (GDNF) requires heparan sulphate glycosaminoglycan. J Cell Sci 115:4495-4503.

Brushart T M, Gerber J, Kessens P, Chen Y G, Royall R M (1998) Contributions of pathway and neuron to preferential motor reinnervation. J Neurosci 18:8674-8681.

Chew S Y, Wen J, Yim E K, Leong K W (2005) Sustained release of proteins from electrospun biodegradable fibers. Biomacromolecules 6:2017-2024.

Chew S Y, Mi R, Hoke A, Leong K W (2007) Aligned protein-polymer composite fibers enhance nerve regeneration: A potential tissue engineering platform. Advanced Functional Materials 17:1288-1296, Chua K N, Chai C, Lee P C, Ramakrishna S, Leong K W, Mao H Q (2007) Functional nanofiber scaffolds with different spacers modulate adhesion and expansion of cryopreserved umbilical cord blood hematopoietic stem/progenitor cells. Exp Hematol 35:771-781.

Fischer S E, Liu X, Mao H Q, Harden J L (2007) Controlling cell adhesion to surfaces via associating bioactive triblock proteins. Biomaterials 28:3325-3337.

Hoke A, Redett R, Hameed H, Jari R, Thou C, Li Z B, Griffin J W, Brushart T M (2006) Schwann cells express motor and sensory phenotypes that regulate axon regeneration. J Neurosci 26:9646-9655.

Jiang X S, Chai C, Zhang Y, Zhuo R X, Mao H Q, Leong K W (2006) Surface immobilization of adhesion peptides on substrate for ex vivo expansion of cryopreserved umbilical cord blood CD34+ cells. Biomaterials 27:2723-2732.

Madison R D, Archibald S J, Brushart T M (1996) Reinnervation accuracy of the rat femoral nerve by motor and sensory neurons. J Neurosci 16:5698-5703, Mi R, Chen W, Hoke A (2007) Pleiotrophin is a neurotrophic factor for spinal motor neurons. Proc Natl Acad Sci USA 104:4664-4669.

Redett R, Jari R, Crawford T, Chen Y G, Rohde C, Brushart T M (2005) Peripheral pathways regulate motoneuron collateral dynamics. J Neurosci 25:9406-9412.

Rider C C (2006) Heparin/heparan sulphate binding in the TGF-beta cytokine superfamily. Biochem Soc Trans 34:458-460.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A nerve guide for peripheral nerve regeneration comprising:
an outer biodegradable poly(ε-caprolactone) (PCL) membrane which forms an external surface of a hollow body in the form of a tube;
a cross-linked hydrogel layer comprising polyvinyl alcohol (PVA) and poly(ethylene glycol) (PEG) in an IPN network comprising glial cell-derived neurotrophic factor (GDNF), wherein an external surface of the cross-linked hydrogel layer is coupled to an internal surface of the outer biodegradable PCL membrane; and a surface-functionalized nanofiber layer comprising electrospun fibers and a surface-tethered laminin coating, and wherein the surface-functionalized nanofiber layer is coupled to an internal surface of the cross-linked hydrogel layer to form an internal surface that defines a lumen of the hollow body.

2. The nerve guide of claim 1, wherein the cross-linked hydrogel layer comprises GDNF and BDNF or GDNF and NT3.

3. The nerve guide of claim 1, wherein the surface-functionalized nanofiber layer is further coated with heparin.

4. The nerve guide of claim 1, wherein the nanofiber layer comprises laminin and heparin.

5. The nerve guide of claim 1, wherein the outer biodegradable PCL membrane is between about 50 and about 1000 μm thick.

6. The nerve guide of claim 1, wherein the outer biodegradable PCL membrane is porous.

7. The nerve guide of claim 1, wherein the cross-linked hydrogel layer further comprises a pluronic polymer, heparin, heparan sulfate, chitosan, alginate, or dextran sulfate.

8. The nerve guide of claim 1, wherein a thickness of the cross-linked hydrogel layer is between about 200 µm and about 1.5 mm in a swollen state.

9. The nerve guide of claim 1, wherein the surface functionalized nanofiber layer comprises one or more natural or synthetic biocompatible polymers comprising polymer fibers selected from the group consisting of biodegradable polyesters, proteins, and polysaccharides.

10. The nerve guide of claim 9, wherein the one or more polymer fibers comprise a polyester or derivative thereof.

11. The nerve guide of claim 9, wherein the polymer fibers comprise collagen or laminin.

12. The nerve guide of claim 9, wherein the one or more polymer fibers comprise chondroitin sulfate, alginate or derivatives thereof.

13. The nerve guide of claim 9, wherein the one or more polymer fibers comprise polylactide, polyglycolide, polycaprolactone or copolymers thereof.

14. The nerve guide of claim 9, wherein an average fiber diameter is between about 10 nm and 10 µm.

15. The nerve guide of claim 9, wherein an average fiber diameter is between about 100 nm and 1 µm.

16. The nerve guide of claim 1, wherein the electrospun fibers are randomly oriented fibers.

17. The nerve guide of claim 1, wherein the electrospun fibers are aligned fibers.

18. The nerve guide of claim 1, wherein the GDNF is present in a gradient of lower concentration to higher concentration from a proximal end of the nerve guide to a distal end of the nerve guide.

19. The nerve guide of claim 1, wherein the nanofiber layer further comprises a Schwann cell.

20. A method of treating peripheral nerve or spinal cord injury comprising: surgically implanting the nerve guide of any one of claims 1, 2, 3, 4, 5-13, 16-18 or 19 at a site of a nerve injury; thereby treating peripheral nerve or spinal cord injury.

21. The method of claim 20, wherein the nerve guide comprises cells selected from the group consisting of autologous Schwann cells, Schwann cells derived from human pluripotent stem cells, and Schwann cells derived from adult stem cells.

22. The method of claim 21, wherein the Schwann cells are derived from human induced pluripotent stem cells or human embryonic stem cells.

23. The method of claim 21, wherein the Schwann cells are derived from allogenic or autologous mesenchymal stem cells.

* * * * *